United States Patent [19]

Asano

[11] Patent Number: Plant 7,093

[45] Date of Patent: Jan. 2, 1990

[54] LILY PLANT NAMED ROTE HORN

[75] Inventor: Yoshito Asano, Tsukuba, Japan

[73] Assignee: Hokkaido University, Sapporo, Japan

[21] Appl. No.: 306,992

[22] Filed: Feb. 7, 1989

[51] Int. Cl.[4] ..... H01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A lily named Rote Horn having flowers generally similar in shape to but smaller than cultivars of *L. longiflorum,* a distinctive pink flower color unknown to *L. longiflorum* cultivars, early flowering, resistant to fading, shiny dark green leaves, and triploid and infertile habit.

1 Drawing Sheet

1

The present invention comprises a new and distinct interspecific hybrid cultivar of lily, botanically known as Lilium, and hereinafter referred to by the vultivar name Rote Horn.

Rote Horn is a product of a planned breeding program which had the objective of creating new lily cultivars having pink flowers shaped similarly to the flower of *Lilum longiflorum.* No previous *L. longiflorum* existed having pink flower color, at least to the knowledge of the inventor. Although pink varieties of the species *L. rubellum* and *L. japonicum* do exist, these species are rather difficult to grow. The breeding efforts were directed at retaining the *L. longiflorum* shape, and creating pink flower color. This was accomplished by crossing the relatively distant species *L. longiflorum* and *L. elegans.*

Rote Horn was originated from a hybridization made in a controlled breeding program in Sapporo, Hokkaido, Japan by the inventor in approximately 1974. The female parent was a *L. longiflorum* cultivar not specifically identifiable at this time. The male parent of Rote Horn was a cultivar created by crossing *L. elegans* c.v. Enchantment and *L. elegans* c.v. Taisho Beni.

Rote Horn was discovered and selected as one flowering plant within the progeny of the stated cross by the inventor in 1976 in a controlled environment in Sapporo, Hokkaido, Japan.

The first act of asexual reproduction of Rote Horn was accomplished when propagation of tissue culture was taken from the initial selection in October 1984 by applicant in a controlled environment in Kobuchizawa, Yamanashi, Japan.Horticultural examination of selected units initiated in March 1985 has demonstrated that the combination of characteristics as herein disclosed for Rote Horn are firmly fixed and are retained through successive generations of asexual reproduction.

Rote Horn has not been observed under all possible environmental conditions. The phenotype may vary significantly with variations in environment such as temperature, light intensity, and day length. The following observations, measurements, and comparisons describe plants grown in Kobuchizawa, Yamanashi, Japan under greenhouse conditions which approximate those generally used in commercial practice.

The following traits have been repeatedly observed and are determined to be basic characteristics of Rote Horn which in combination distinguish this lily as a new and distinct cultivar.

2

1. Rote Horn has pink flowers shaped similar to cultivars of *L. longiflorum,* but smaller. The plant height is approximately 70–80 cm.
2. Rote Horn is an early flowering type lily, flowering between June 25–July 5 outdoors at approximately 800 meters above sea level.
3. Vase life is excellent. The pink flower color does not fade out even as a cut flower.
4. Rote Horn produces may bulblets, and scaling is very easy.
5. It is triploid and infertile.
6. Leaves are shiny dark green and high in ornamental value.

Of the many commercial cultivars known to the present inventor, the most similar in comparison to Rote Horn are *L. longiflorum* cultivars. In comparison to these, Rote Horn has pink flowers which have not been previously available in this species. In addition, Rote Horn is a triploid and infertile, and the size of its flowers are smaller than the control variety of *L. longiflorum.*

The accompanying photographic drawing shows typical flower characteristics of Rote Horn, with colors being as true as possible with illustrations of this type.

In the following description, color references are made to The Royal Horticultural Society Colour Chart (RHS). The color values were determined at approximately 4:00 p.m. on May 20, 1988 at Miyoshi Yatsugatake Research Farm, Kobuchizawa, Yamanashi, Japan.

THE PLANT

Origin: Seedling from embryo culture.

Parentage:

*Seed parent.*—*Lilium longiflorum.*

*Pollen parent.*—*Lilium elegans* "Utagoe".

Classification:

*Botanic.*—Hybrid lilium clone.

*Commercial.*—Interspecific hybrid lily.

Form: Single stem.

Height: 70–80 cm. when produced from bulbs 8 to 10 cm. in circumference.

Growth habit: Vigorous, sturdy and upright.

Strength: Excellent.

Foilage:

*Quantity.*—Moderate, approximately 50 leaves.

*Size of leaf.*—10–12 cm. long.

*Shape of leaf.*—Lanceolate.

*Texture.*—Smooth and glossy.

*Color.*—Brilliant dark green.

Bulbs:

*Size.*—Varying sizes ranging up to 20 cm in circumference.

*Color.*—White with yellow overtone.

THE BUD

Form: Long, ovoid and pointed.

Size: 12–15 cm.

Opening: Normal, same as *Lilium longiflorum.*

Color: 71B.

Tepals: Dark pink outside.

THE FLOWER

Blooming habit: Annually, blooming profusely from the end of June to the beginning of July.

Size: Medium; 12–14 cm. in diameter.

Borne: 1–6 or more flowers depending on the bulb size.

Shape: Trumpet shape.

Tepalage:

*Number of tepals.13* Six.

*Arrangement.*—Imbricated or overlapped.

*Color of upper surface.*—62C.

*Color of lower surface.*—66D.

*Tepal longevity.*—2–3 weeks depending upon environmental temperature.

*Spotting.*—None.

Peduncle:

*Length.*—6–8 cm.

*Color.*—Light green.

*Form.*—Sturdy and upright, angled about 30° from vertical.

Texture: Soft.

Appearance: Velvety.

Fragrance: Slight.

Lasting quality: The flower is long lasting both on the plant and as a cut flower.

REPRODUCTIVE ORGANS

Stamens, anthers:

*Arrangements.*—Typical of liliaceae.

*Number.*—Six.

Filaments.—11 mm, soft green.

Pollens and anthers: Reddish brown in color.

Pistils: One in number.

Stigma: Yellow in color.

FRUIT

Fertility: Rote Horn is triploid and infertile.

I claim:

1. A new and distinct cultivar of lily named Rote Horn, as illustrated and described.

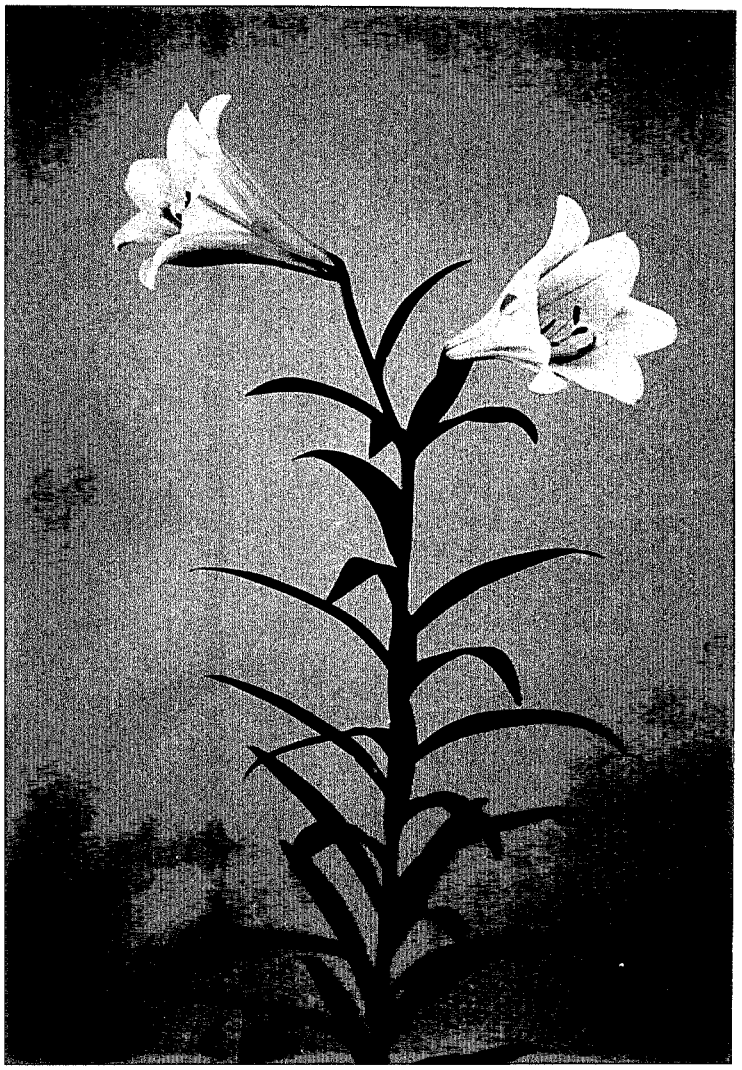

* * * * *